United States Patent
Xia

(10) Patent No.: US 7,192,937 B2
(45) Date of Patent: Mar. 20, 2007

(54) OLIGOSACCHARIDE-CONTAINING COMPOSITIONS AND USES THEREOF

(75) Inventor: Erning Xia, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 129 days.

(21) Appl. No.: 10/848,848

(22) Filed: May 19, 2004

(65) Prior Publication Data

US 2005/0260098 A1   Nov. 24, 2005

(51) Int. Cl.
    *A61K 31/715*   (2006.01)
(52) U.S. Cl. ............................. 514/54; 514/53; 514/61; 536/124
(58) Field of Classification Search ................... 514/54, 514/53, 61; 536/124
    See application file for complete search history.

(56) References Cited

U.S. PATENT DOCUMENTS

| | | | |
|---|---|---|---|
| 4,748,158 A | 5/1988 | Biermann et al. | 514/25 |
| 6,448,062 B1 | 9/2002 | Huth et al. | 435/264 |
| 6,491,840 B1 * | 12/2002 | Frankenbach et al. | 252/8.91 |
| 6,613,733 B1 * | 9/2003 | Barnabas et al. | 510/470 |

FOREIGN PATENT DOCUMENTS

| | | |
|---|---|---|
| EP | 0 042 075 A | 12/1981 |
| EP | 0 409 076 A | 1/1991 |
| EP | 0 923 950 A | 6/1999 |
| WO | WO01/57172 A | 8/2001 |
| WO | WO2004/030709 A | 4/2004 |

OTHER PUBLICATIONS

Gruber, James V. et al "Examination of a New Cationic Maltose Oligosaccharides and Its Effect on Skin Moisturization and Hair Conditioning" Cosmetic News, vol. 26, No. 148, 2003, pp. 44-45, XP009059477, p. 44-p. 45.

* cited by examiner

*Primary Examiner*—Shaojia Anna Jiang
*Assistant Examiner*—Everett White
(74) *Attorney, Agent, or Firm*—Paul T. Lavoie

(57) ABSTRACT

The use of compositions containing one or more oligosaccharides in an amount effective to disinfect and/or preserve medical devices, pharmaceutical preparations, and the like is described. Buffered solutions containing one or more oligosaccharide-containing compositions and methods of making and using the same are also described.

40 Claims, No Drawings

OLIGOSACCHARIDE-CONTAINING COMPOSITIONS AND USES THEREOF

FIELD OF THE INVENTION

The present invention is directed toward the use of one or more oligosaccharides in a composition useful for disinfection and/or preservation. More particularly, the present invention is directed toward the use of one or more oligosaccharides in a buffered solution useful for no-rub cleaning of contact lenses and for preservation of ophthalmic solutions and devices.

BACKGROUND OF THE INVENTION

Contact lenses in wide use today fall into two general categories, hard and soft. The hard or rigid corneal type lenses are formed from materials prepared by the polymerization of acrylic esters, such as poly(methyl methacrylate) (PMMA). The gel, hydrogel or soft type lenses are made by polymerizing such monomers as 2-hydroxyethyl methacrylate (HEMA) or, in the case of extended wear lenses, by polymerizing silicon-containing monomers or macromonomers. Both the hard and soft types of contact lenses are exposed to a broad spectrum of microbes during normal wear and become soiled relatively quickly. Contact lenses whether hard or soft therefore require routine cleaning and disinfecting. Failure to routinely clean and disinfect contact lenses properly can lead to a variety of problems ranging from mere discomfort when being worn to serious ocular infections. Ocular infections caused by virulent microbes such as *Pseudomonas aeruginosa* can lead to loss of the infected eye(s) if left untreated or if allowed to reach an advanced stage before initiating treatment.

U.S. Pat. No. 4,758,595 discloses a contact lens disinfectant and preservative containing a biguanide or a water-soluble salt thereof in combination with a buffer, preferably a borate buffer, e.g., boric acid, sodium borate, potassium tetraborate, potassium metaborate or mixtures of the same.

U.S. Pat. No. 4,361,548 discloses a contact lens disinfectant and preservative containing dilute aqueous solutions of a polymer; namely, dimethyldiallylammonium chloride (DMDAAC) having molecular weights ranging from about 10,000 to 1,000,000. Amounts of DMDAAC homopolymer as low as 0.00001 percent by weight may be employed when an enhancer, such as thimerosal, sorbic acid or phenylmercuric salt is used therewith. Although lens binding and concomitant eye tissue irritation with DMDAAC were reduced, it was found in some users to be above desirable clinical levels.

Despite the availability of various commercially available contact lens disinfecting systems such as heat, hydrogen peroxide, biguanides, polymeric biguanides, quaternary ammonium polyesters, amidoamines and other chemical agents, there continues to be a need for improved disinfecting systems. Such improved disinfecting systems include systems that are simple to use, are effective against a broad spectrum of microbes, are non-toxic and do not cause ocular irritation as the result of binding to the contact lens material. There is a particular need in the field of contact lens disinfection and ophthalmic composition preservation for safe and effective chemical agents with antimicrobial activity.

SUMMARY OF THE INVENTION

The present invention relates to compositions useful for no-rub cleaning of contact lenses, for disinfecting medical devices such as contact lenses, for preserving solutions such as ophthalmic solutions, pharmaceutical preparations, artificial tears and comfort drops against microbial contamination, and for preserving medical devices such as contact lenses. Compositions of the present invention are suitable for use with all types of contact lenses, including rigid permeable contact lenses. Compositions of the present invention formulated into a buffered no-rub contact lens cleaning solution eliminates the need for user rubbing of the contact lens during cleaning and provides rapid disinfection of the contact lens. No-rub cleaning and rapid disinfection of contact lenses leads to higher user compliance and greater universal appeal than traditional contact lens disinfecting and cleaning solutions.

The subject oligosaccharide-containing compositions are effective in the manufacture of solutions that are simple to use and do not cause ocular irritation.

Accordingly, it is an object of the present invention to provide compositions useful in the manufacture of medical device disinfecting systems.

Another object of the present invention is to provide a method for using compositions in the disinfection of medical devices.

Another object of the present invention is to provide compositions useful in ophthalmic systems for disinfecting contact lenses.

Another object of the present invention is to provide compositions useful in preserving ophthalmic systems from microbial contamination.

Another object of the present invention is to provide compositions useful in ophthalmic systems for disinfecting contact lenses with reduced or eliminated eye irritation.

Another object of the present invention is to provide a method of making compositions useful in ophthalmic systems.

Still another object of the present invention is to provide a method of making compositions useful as disinfecting and preservative agents.

These and other objectives and advantages of the present invention, some of which are specifically described and others that are not, will become apparent from the detailed description and claims that follow.

DETAILED DESCRIPTION OF THE INVENTION

Compositions of the present invention can be used with all contact lenses such as conventional hard and soft lenses, as well as rigid and soft gas permeable lenses. Such suitable lenses include both hydrogel and non-hydrogel lenses, as well as silicone and fluorine-containing lenses. The term "soft contact lens" as used herein generally refers to those contact lenses that readily flex under small amounts of force. Typically, soft contact lenses are formulated from polymers having a certain proportion of repeat units derived from monomers such as 2-hydroxyethyl methacrylate and/or other hydrophilic monomers, typically crosslinked with a crosslinking agent. However, newer soft lenses, especially for extended wear, are being made from high-Dk silicone-containing materials.

Compositions of the present invention comprise one or more cationic, anionic or nonionic oligosaccharides. "Oligosaccharide" as used herein is a carbohydrate containing from two to ten simple sugars linked together. Such oligosaccharide-containing compositions of the present invention contain from about 0.0001 to about 10 weight percent, but preferably from about 0.001 to about 5 weight percent and most preferably from about 0.001 to about 2.5 weight percent of one or more oligosaccharides based on the total weight of the composition for disinfection, or to achieve an effective "disinfecting amount". Such oligosaccharide-containing compositions of the present invention contain from about 0.0001 to about 10 weight percent, but preferably from about 0.001 to about 5 weight percent and most preferably from about 0.001 to about 0.1 weight percent of one or more oligosaccharides based on the total weight of the composition for preservation, or to achieve an effective "preservative amount". Suitable oligosaccharides include for example but are not limited to quaternized oligosaccharides such as for example but not limited to stearyl dihydroxypropyldimonium oligosaccharide (SDO) available commercially under the trade name Oligoquat M™ from Arch Personal Care Product, South Plainfield, N.J. Preferred oligosaccharides for use in the present invention have an average molecular weight ranging from about 10,000 to about 75,000, but more preferable from about 20,000 to about 60,000 and most preferably from about 25,000 to about 50,000. The preferred oligosaccharide for use in the present invention is stearyl dihydroxypropyldimonium oligosaccharide (SDO). The average molecular weight of stearyl dihydroxypropyldimonium oligosaccharide is 25,000 to 50,000. Stearyl dihydroxypropyidimonium oligosaccharide is the preferred oligosaccharide for use in compositions of the present invention due to its extensive moisture-binding properties and excellent substantivity, which serve to moisturize and soften ocular and/or nasal tissues, thus, increasing user comfort.

The oligosaccharide-containing compositions of the present invention are useful for disinfecting medical devices and/or preserving pharmaceutical solutions, ophthalmic systems or medical devices. For example, the subject oligosaccharide-containing compositions are useful in contact lens care solutions for rapidly disinfecting contact lenses. For purposes of the present invention, "rapidly disinfecting" or "rapid disinfection" as used herein means microorganism reduction of at least one log in about one hour. Compositions of the present invention are preferably in solution in sufficient concentration to destroy harmful microorganisms on the surface of a contact lens within a recommended minimum soaking time. This recommended minimum soaking time is included in the package instructions for use of the solution. The term "disinfecting solution" does not exclude the possibility that the solution may also be useful as a preserving solution, or that the disinfecting solution may be useful for other purposes such as daily no-rub cleaning, rinsing, and/or storage of contact lenses, depending on the particular formulation containing the subject compositions. Additionally, compositions of the present invention can be used in conjunction with other known disinfecting or preserving compounds if desired.

One or more compositions of the present invention in solution are physiologically compatible or "ophthalmically safe" for use with contact lenses. Ophthalmically safe as used herein means that a contact lens treated with or in the subject solution is generally suitable and safe for direct placement on the eye without rinsing. The subject solutions are safe and comfortable for daily contact with the eye via a contact lens that has been wetted with the solution. An ophthalmically safe solution has a tonicity and pH that is compatible with the eye and comprises materials, and amounts thereof, that are non-cytotoxic according to ISO (International Standards Organization) standards and U.S. FDA (Food and Drug Administration) regulations. The solution should be sterile in that the absence of microbial contaminants in the product prior to release should be statistically demonstrated to the degree necessary for such products.

In addition to one or more oligosaccharides, compositions of the present invention may also include one or more aminoalcohol buffers, such as ethanolamine buffers, present in a total amount of from approximately 0.02 to approximately 3.0 percent by weight based on the total weight of the composition. Suitable aminoalcohol buffers include for example but are not limited to monoethanolamine (MEA), diethanolamine (DEA), triethanolamine (TEA), 2-amino-2-methyl-1,3-propanediol (AMPD), 2-dimethylamino-2-methyl-1-propanediol (DMAMP), 2-amino-2-ethylpropanol (AEP), 2-amino-1-butanol (AB) and 2-amino-2-methyl-1-propanol (AMP), but preferably MEA, DEA or TEA.

In addition to or instead of possibly one or more aminoalcohol buffers, the subject compositions may likewise include one or more buffers, or a buffering system to adjust the final pH of a solution containing said compositions. Suitable buffers include for example but are not limited to phosphate buffers, borate buffers, citrate buffers tris(hydroxymethyl)aminomethane (Tris) buffers, bis(2-hydroxyethyl)imino-tris(hydroxymethyl)methane (bis-Tris) buffers, sodium bicarbonate, and combinations thereof. A suitable buffering system for example may include at least one phosphate buffer and at least one borate buffer, which buffering system has a buffering capacity of 0.01 to 0.5 mM, preferably 0.03 to 0.45, of 0.01 N of HCl and 0.01 to 0.3, preferably 0.025 to 0.25, of 0.01 N of NaOH to change the pH one unit. Buffering capacity is measured by a solution of the buffers only. The pH of lens care solutions of the present invention is preferably maintained within the range of 5.0 to 8.0, more preferably about 6.0 to 8.0, most preferably about 6.6 to 7.6.

Compositions of the present invention may likewise include one or more tonicity agents to approximate the osmotic pressure of normal lachrymal fluids, which is equivalent to a 0.9 percent solution of sodium chloride or 2.5 percent glycerin solution. Examples of suitable tonicity agents include but are not limited to sodium and potassium chloride, dextrose, mannose, glycerin, calcium and magnesium chloride. These agents are typically used individually in amounts ranging from about 0.01 to about 3.0 percent w/v and, preferably, from about 0.2 to about 1.5 percent w/v. Preferably, the tonicity agent is employed in an amount to provide a final osmotic value of about 200 to about 450 mOsm/kg and more preferably between about 200 to about 350 mOsm/kg, and most preferably between about 200 to about 320 mOsm/kg.

The compositions of the present invention are described in still greater detail in the examples that follow.

EXAMPLE 1

Preparation of Test Sample Solutions

Sample solutions for testing were prepared in accordance with formulations of the present invention set forth below in Table 1.

TABLE 1

Test Sample Solutions

| Ingredients | Sample | | | | |
|---|---|---|---|---|---|
| W/W Percent | 1 | 2 | 3 | 4 | 5 |
| Triethanolamine HCl | 0.934 | 0.934 | 0.934 | 0.934 | 0.934 |
| Triethanolamine BASE | 0.145 | 0.145 | 0.145 | 0.145 | 0.145 |
| Sodium Chloride | 0.34 | 0.34 | 0.34 | 0.34 | 0.34 |
| SDO | 0.10 | 0.05 | 0.025 | 0.0125 | 0.00625 |
| pH | 7.15 | 7.15 | 7.15 | 7.16 | 7.15 |
| Osmolality (mOsm/Kg) | 211 | 210 | 210 | 209 | 211 |

EXAMPLE 2

Biocidal Testing of Test Samples with Five of FDA/ISO Challenge Microorganisms

Test solutions prepared in accordance with Example 1 above, were each tested for ISO/FDA microbial biocidal efficacy using five FDA/ISO challenge microorganisms, i.e., three bacteria and two fungi. Primary acceptance criteria established for bacteria require that the number of viable bacteria, recovered per ml, shall be reduced by a value not less than 3.0 logs within the minimum recommended disinfection period. Primary acceptance criteria established for yeasts and molds require that the number of viable yeasts and molds, recovered per ml, shall be reduced by a value of not less than 1.0 logs within the minimum recommended disinfection time with no increase at not less than four times the minimum recommended disinfection time within an experimental error of +/−0.5 logs. Secondary acceptance criteria for bacteria requires that there is a combined log reduction for the mean values of all three bacteria of not less than 5.0 logs within the recommended disinfection period. The minimum acceptable mean log reduction for any single bacterial type is 1.0 log. Stasis for the yeast and mold must be observed for the minimum recommended disinfection period. Results of the ISO/FDA microbial biocidal efficacy testing of the subject test solutions are set forth below in Table 2. The results set forth in Table 2, illustrate that the sample solutions containing 0.01 w/w percent or more oligosaccharide, i.e., samples 1, 2, 3 and 4, passed ISO/FDA microbial biocidal efficacy standards. Sample solution 5, containing 0.006 w/w percent oligosaccharide, did not pass ISO/FDA microbial biocidal efficacy standards.

TABLE 2

Biocidal Efficacies With 10 Percent Organic Soil

| ISO Agent | Hours | Log Reduction of Sample | | | | |
|---|---|---|---|---|---|---|
| | | 1 | 2 | 3 | 4 | 5 |
| *Staphylococcus aureus* | | | | | | |
| (ATCC 6538) | 1 | >4.5 | >4.5 | >4.5 | 4.5 | 4.7 |
| | 4 | >4.5 | >4.5 | >4.5 | >4.7 | >4.7 |
| *Pseudomonas aeruginosa* | | | | | | |
| (ATCC 9027) | 1 | >4.7 | >4.7 | >4.7 | 2.6 | ND |
| | 4 | >4.7 | >4.7 | >4.7 | >4.8 | 2.9 |

TABLE 2-continued

Biocidal Efficacies With 10 Percent Organic Soil

| ISO Agent | Hours | Log Reduction of Sample | | | | |
|---|---|---|---|---|---|---|
| | | 1 | 2 | 3 | 4 | 5 |
| *Serratia marcescens* | | | | | | |
| (ATCC 13880) | 1 | >4.6 | 4.3 | 3.8 | 2.8 | 2.0 |
| | 4 | >4.6 | >4.6 | >4.6 | 4.2 | 3.0 |
| *Candida albicans* | | | | | | |
| (ATCC 10231) | 1 | >4.6 | >4.6 | 3.6 | 2.4 | 0.8 |
| | 4 | >4.6 | >4.6 | >4.6 | >4.7 | 2.0 |
| *Fusarium solani* | | | | | | |
| (ATCC 36031) | 1 | >4.5 | 3.6 | >4.5 | 3.6 | 1.2 |
| | 4 | >4.5 | >4.5 | >4.5 | 4.1 | 2.3 |

ND = No data

Oligosaccharide containing compositions of the present invention are useful as contact lens care solutions for no-rub cleaning and rapid disinfection of contact lenses. A disinfecting amount of oligosaccharide is an amount that will at least partially reduce the microorganism population in the formulations employed. Preferably, a disinfecting amount is that which will reduce the microbial burden of representative bacteria by two log orders in four hours and more preferably by one log order in one hour. Most preferably, a disinfecting amount is an amount that will eliminate the microbial burden on a contact lens when used according to its regimen for the recommended soaking time as established by ISO (International Standards for Ophthalmic Optics)/FDA Stand-Alone Procedures for Disinfection Test (ISO/DIS 14729; 2001). Typically, such agents are present in concentrations ranging from about 0.00001 to about 0.5 percent weight/volume (w/v), and more preferably, from about 0.001 to about 0.5 percent w/v.

As stated above, contact lenses are cleaned without the need for manual rubbing and rapidly disinfected by contacting the lens with a solution of one or more compositions of the present invention. This is accomplished by simply soaking or immersing a contact lens in several milliliters of the subject solution. Preferably, the lens is permitted to soak in the solution for a period of at least one to four hours. The lenses are then removed from the solution, rinsed with the same or a different solution, for example a preserved isotonic saline solution and then replaced on the eye.

Solutions containing one or more compositions of the present invention may be formulated into specific contact lens care products for use as customary in the field of ophthalmology. Such products include but are not limited to wetting solutions, soaking solutions, cleaning and conditioning solutions, as well as multipurpose-type lens care solutions and in-eye cleaning and conditioning solutions.

Solutions containing one or more compositions of the present invention may be formulated into specific products for disinfecting medical devices such as for example but not limited to contact lenses.

Products containing one or more compositions of the present invention may be formulated for preservation against microbial contamination such as for example but not limited to ophthalmic solutions, pharmaceuticals, artificial tears and comfort drops.

Solutions containing one or more compositions of the present invention may be formulated into specific products for preserving medical devices from microbial contamination such as for example but not limited to products formulated for the storage of contact lenses.

While the invention has been described in conjunction with specific examples thereof, this is illustrative only. Accordingly, many alternatives, modifications, and variations will be apparent to those skilled in the art in the light of the foregoing description and it is, therefore, intended to embrace all such alternatives, modifications, and variations as to fall within the spirit and scope of the appended claims.

We claim:

1. A composition comprising:
   an effective disinfecting amount of stearyl dihydroxypropyldimonium oligosaccharide in an ophthalmically acceptable aqueous solution.

2. The composition of claim 1 wherein said effective disinfecting amount is about 0.0001 to about 10 weight percent.

3. The composition of claim 1 further comprising one or more aminoalcohol buffers and one or more tonicity agents.

4. The composition of claim 3 wherein said one or more aminoalcohol buffers
   are selected from the group consisting of monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

5. The composition of claim 3 wherein said one or more aminoalcohol buffers
   are present in about 0.02 to about 3.0 percent by weight.

6. The composition of claim 3 wherein said one or more tonicity agents are
   selected from the group consisting of sodium chloride, potassium chloride, dextrose, mannose, glycerin, calcium chloride and magnesium chloride.

7. The composition of claim 3 wherein said one or more tonicity agents are
   present in about 0.01 to about 3.0 percent by weight.

8. The composition of claim 3 wherein said one or more tonicity agents are
   present in an amount to provide a final osmotic value of about 200 to about 450 mOsm/kg.

9. A method of producing the composition of claim 1 comprising:
   combining an effective disinfecting amount of stearyl dihydroxypropyldimonium oligosaccharide with water to form a solution, wherein the solution is ophthalmically safe.

10. The method of claim 9 wherein said effective disinfecting amount is about 0.0001 to about 10 weight percent.

11. The method of claim 9 further comprising one or more aminoalcohol buffers and one or more tonicity agents.

12. The method of claim 9 further comprising one or more aminoalcohol buffers and one or more tonicity agents wherein said one or more aminoalcohol buffers are selected from the group consisting of monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

13. The method of claim 9 further comprising one or more aminoalcohol buffers and one or more tonicity agents wherein said one or more aminoalcohol buffers are present in about 0.02 to about 3.0 percent by weight.

14. The method of claim 9 further comprising one or more aminoalcohol buffers and one or more tonicity agents wherein said one or more tonicity agents are selected from the group consisting of sodium chloride, potassium chloride, dextrose, mannose, glycerin, calcium chloride and magnesium chloride.

15. The method of claim 9 further comprising one or more aminoalcohol buffers and one or more tonicity agents wherein said one or more tonicity agents are present in about 0.01 to about 3.0 percent by weight.

16. The method of claim 9 further comprising one or more aminoalcohol buffers and one or more tonicity agents wherein said one or more tonicity agents are present in an amount to provide a final osmotic value of about 200 to about 450 mOsm/kg.

17. The method of claim 9 further comprising one or more aminoalcohol buffers and one or more tonicity agents wherein an additional buffer or buffering system is present.

18. A solution comprising an amount of stearyl dihydroxypropyldimonium oligosaccharide and water wherein the solution is ophthalmically safe.

19. The solution of claim 18 wherein said effective disinfecting amount is about 0.0001 to about 10 weight percent.

20. The solution of claim 18 further comprising one or more aminoalcohol buffers and one or more tonicity agents.

21. The solution of claim 18 further comprising one or more aminoalcohol buffers and one or more tonicity agents wherein said one or more aminoalcohol buffers are selected from the group consisting of monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

22. The solution of claim 18 further comprising one or more aminoalcohol buffers and one or more tonicity agents wherein said one or more aminoalcohol buffers are present in about 0.02 to about 3.0 percent by weight.

23. The solution of claim 18 further comprising one or more aminoalcohol buffers and one or more tonicity agents wherein said one or more tonicity agents are selected from the group consisting of sodium chloride, potassium chloride, dextrose, mannose, glycerin, calcium chloride and magnesium chloride.

24. The solution of claim 18 further comprising one or more aminoalcohol buffers and one or more tonicity agents wherein said one or more tonicity agents are present in about 0.01 to about 3.0 percent by weight.

25. The solution of claim 18 further comprising one or more aminoalcohol buffers and one or more tonicity agents wherein said one or more tonicity agents are present in an amount to provide a final osmotic value of about 200 to about 450 mOsm/kg.

26. The solution of claim 18 further comprising one or more aminoalcohol buffers and one or more tonicity agents wherein an additional buffer or buffering system is present.

27. A method of desinfecting a contact lens comprising:
    contacting a contact lens with an ophthalmically safe aqueous solution comprising dihydroxypropyldimonium oligosaccharide for a period of time suitable to reduce or eliminate a microbial burden on said contact lens.

28. A composition for treating a contact lens comprising:
    an effective amount of dihydroxypropyldimonium oligosaccharide in an ophthalmically safe aqueous solution.

29. The composition of claim 28 wherein said effective amount is about 0.0001 to about 10 weight percent.

30. A composition for disinfecting a contact lens comprising:
   a disinfecting amount of dihydroxypropyldimonium oligosaccharide in an ophthalmically safe aqueous solution.

31. The composition of claim 30 wherein said disinfecting amount is about 0.0001 to about 10 weight percent.

32. A composition for preserving a contact lens comprising:
   a preservative amount of dihydroxypropyldimonium oligosaccharide in an ophthalmically safe aqueous solution.

33. The composition of claim 32 wherein said preservative amount is about 0.0001 to about 10 weight percent.

34. The composition of claim 28, 30 or 32 further comprising one or more aminoalcohol buffers and one or more tonicity agents.

35. The composition of claim 28, 30 or 32 further comprising one or more aminoalcohol buffers selected from the group consisting of monoethanolamine, diethanolamine, triethanolamine, 2-amino-2-methyl-1,3-propanediol, 2-dimethylamino-2-methyl-1-propanediol, 2-amino-2-ethylpropanol, 2-amino-1-butanol and 2-amino-2-methyl-1-propanol.

36. The composition of claim 28, 30 or 32 further comprising one or more aminoalcohol buffers present in about 0.02 to about 3.0 percent by weight.

37. The composition of claim 28, 30 or 32 further comprising one or more tonicity agents selected from the group consisting of sodium chloride, potassium chloride, dextrose, mannose, glycerin, calcium chloride and magnesium chloride.

38. The composition of claim 28, 30 or 32 further comprising one or more tonicity agents present in about 0.01 to about 3.0 percent by weight.

39. The composition of claim 28, 30 or 32 further comprising one or more tonicity agents present in an amount to provide a final osmotic value of about 200 to about 450 mOsm/kg.

40. The composition of claim 28, 30 or 32 further comprising a buffer or buffering system.

* * * * *